United States Patent [19]

McCulloch et al.

[11] Patent Number: 5,071,560

[45] Date of Patent: Dec. 10, 1991

[54] PROCESS FOR PURIFYING PHENYLALANINE

[75] Inventors: Beth McCulloch, Barrington; Walter H. Goodman, Villa Park, both of Ill.

[73] Assignee: UOP, Des Plaines, Ill.

[21] Appl. No.: 631,175

[22] Filed: Dec. 19, 1990

Related U.S. Application Data

[63] Continuation of Ser. No. 380,921, Jul. 17, 1989, abandoned, which is a continuation-in-part of Ser. No. 260,105, Oct. 20, 1988, abandoned.

[51] Int. Cl.$^5$ .............................................. B01D 15/08
[52] U.S. Cl. .................... 210/635; 210/656; 435/108; 562/443
[58] Field of Search ...................... 562/443; 435/108; 210/635, 656

[56] References Cited

U.S. PATENT DOCUMENTS

| | | | |
|---|---|---|---|
| 2,985,589 | 5/1961 | Broughton et al. | 210/34 |
| 3,040,777 | 6/1962 | Carson et al. | 137/625.15 |
| 3,422,848 | 1/1969 | Liebman et al. | 137/625.15 |
| 3,663,467 | 5/1972 | Albright | 260/2.5 B |
| 3,706,812 | 12/1972 | De Rosset et al. | 260/674 SA |
| 3,787,317 | 1/1974 | Jaworek | 210/31 C |
| 4,537,763 | 8/1985 | Miyake | 426/658 |
| 4,584,400 | 4/1986 | Otani et al. | 562/443 |
| 4,604,483 | 8/1986 | Kitsukawa et al. | 562/443 |
| 4,616,078 | 10/1986 | Di Marchi | 530/305 |
| 4,642,397 | 2/1987 | Zinnen et al. | 568/934 |

OTHER PUBLICATIONS

Summary Bulletin—Amberlite Polymeric Adsorbents, Rohm & Haas (11 pages), 1978.
Preliminary Technical Notes—Amberlite® XAD-7, Rohm & Haas (13 pages) 1978.

*Primary Examiner*—Ernest G. Therkorn
*Attorney, Agent, or Firm*—Thomas K. McBride; John F. Spears, Jr.; Jack H. Hall

[57] ABSTRACT

A process for the liquid phase adsorptive separation of phenylalanine from a fermentation broth containing phenylalanine salts, carbohydrates, amino acids and organic acids. The feed is contacted, at a pH of 4.5–6.5, with a hydrophobic polar, porous synthetic adsorbent, such as Amberlite XAD-7, whose functional groups have a dipole moment of 1.6–2.0, to selectively adsorb the phenylalanine onto said adsorbent to the substantial exclusion of the other feed components and recovering phenylalanine by desorbing with water, an alcohol, a ketone or an ester.

12 Claims, No Drawings

PROCESS FOR PURIFYING PHENYLALANINE

This is a continuation of copending application Ser. No. 07/380,921 filed on July 17, 1989, which, in turn, is a continuation-in-part of U.S. Ser. No. 260,105, filed Oct. 20, 1988, both now abandoned.

BACKGROUND OF THE INVENTION

1. Field of the Invention

The field of art to which this invention pertains is the solid bed adsorptive separation of phenylalanine. More specifically, the invention relates to a process for separating and recovering L-phenylalanine (hereinafter "phenylalanine") from an aqueous solution such as a fermentation broth employing a synthetic polar adsorbent to selectively adsorb phenylalanine.

2. Description of the Prior Art

Phenylalanine is an essential amino acid and is used in the synthetic production of pharmaceuticals and more recently extensively in the production of "Aspartame", a non-nutritive sweetener sold under the trade name "Nutrasweet". There are several routes to the production of phenylalanine: the fermentation of sugar; the enzymatic conversion of cinnamic acid, hydantoin or other sources, e.g., phenylacetaldehyde. All of these routes produce phenylalanine, together with other reaction products, such as lactic acid, acetic acid, phenyllactic acid, cinnamic acid and hydrocinnamic acid, salts, such as KCl, sugars, other amino acids and organic acids.

In U.S. Pat. No. 4,584,400, a process for separating L-phenylalanine from a fermentation broth by a chromatographic process with non-polar adsorbents, e.g., XAD-2 and XAD-4 is disclosed, where the predominant contaminant is L-tyrosine. However, enormous volumes of water, the desorbent, are required to desorb phenylalanine.

Phenylalanine has also been separated from cinnamic acid, as disclosed in U.S. Pat. No. 4,604,483, utilizing XAD-2, XAD-4, XAD-7 and XAD-8 in the presence of at least 0.1N solution of a salt, e.g., ammonium chloride. In this process, the selectivity of the adsorbent for the two components is reversed due to the greater salting-out effect of ammonium chloride on the cinnamic acid than on the phenylalanine. Thus, phenylalanine is eluted first with substantially no cinnamic acid. Applicant's invention does not rely on the salting-out effect on the selectivity.

U.S. Pat. No. 3,787,317 discloses the use of at least two different chromatographic materials, e.g., dextran-based molecular sieves, usually crosslinked, to separate mixtures which are stated to include phenylalanine.

A technical bulletin (undated) promulgated by Rohm and Haas Company discusses the use of Amberlite XAD-7 in several separations, viz. fatty acids from water or toluene; phenol or m-chlorophenol from water or toluene; proteins from aqueous fluids of biological origin. One of these general suggestions for separations is more specifically disclosed in U.S. Pat. No. 4,616,078, wherein proinsulin-like substances may be separated from impure mixtures obtained by recombinant DNA methodology by adsorption on Amberlite XAD-7 or XAD-8 and elution with acetone or acrylonitrile under specified conditions.

None of the references disclose an effective and economic chromatographic process for separating phenylalanine from a fermentation broth.

The invention herein can be practiced in fixed or moving adsorbent bed systems, but the preferred system for this separation is a countercurrent simulated moving bed system, such as described in Broughton U.S. Pat. No. 2,985,589, incorporated herein by reference. Cyclic advancement of the input and output streams can be accomplished by a manifolding system, which are also known, e.g., by rotary disc valves shown in U.S. Pat. Nos. 3,040,777 and 3,422,848. Equipment utilizing these principals are familiar, in sizes ranging from pilot plant scale (DeRosset U.S. Pat. No. 3,706,812 to commercial scale and flow rates from a few cc's per hour to many thousands of gallons per hour.

The functions and properties of adsorbents and desorbents in a chromatographic separation of liquid components are well known, but for reference thereto, Zinnen et al. U.S. Pat. No. 4,642,397 is incorporated herein.

SUMMARY OF THE INVENTION

The present invention is a process for separating phenylalanine from a fermentation feed comprising phenylalanine, salts, carbohydrates, amino acids and organic acids. The process comprises contacting, at adsorption conditions, the feed mixture, while maintaining the pH of the feed mixture from 4.5 to 6.5, with a hydrophobic, polar, porous synthetic adsorbent, and selectively adsorbing phenylalanine onto said adsorbent to the substantial exclusion of the other feed components and desorbing, under desorption conditions, the phenylalanine with desorbent which comprises water, an alcohol, a ketone or an ester or mixtures thereof.

DETAILED DESCRIPTION OF THE INVENTION

The adsorbent to be used in the process of this invention will comprise a group of specific non-ionic hydrophobic synthetic crosslinked aliphatic polymers. It is not an ion exchange resin since it contains no ionically functional groups, but rather, derives its adsorptive properties from the combination of macroreticular porosity, pore size distribution, high surface area and the aliphatic nature of its structure. A preferred adsorbent in this group is a macroporous, crosslinked acrylic ester copolymer which has intermediate polarity and more specifically, where the functional groups have a dipole moment of 1.8. The nature of adsorbents having intermediate polarity is described in Rohm & Haas' *Summary Bulletin—Amberlite Polymeric Adsorbents*, page 1 and Table 1, page 3. The dipole moment of representative adsorbents is given in Table 2, page 5. However, it is believed that the dipole moment of the group of adsorbents defined above may vary, e.g., from about 1.6 to about 2.0. Typical crosslinking agents (a comonomer) may include divinylbenzene, but polyfunctional aliphatic monomers e.g., methacrylic acid, acrylic acid or derivatives thereof, etc., are preferred. A more preferred adsorbent is a self-crosslinked acrylic ester homopolymer from monomers having polyfunctional groups, i.e., at least three methacrylate groups, capable of self-crosslinking, e.g., trimethylolpropane trimethacrylate and pentaerythritol tetramethacrylate, etc. XAD-8 is a copolymer of methyl acrylate and trimethylolpropane trimethacrylate. Examples of self-crosslinking polyfunctional monomers include the aforementioned trimethylolpropane trimethacrylate. The preferred copolymers and homopolymers and the method of making them are disclosed in U.S. Pat. No. 3,663,467, incorporated herein by reference.

As previously stated, there are several synthetic routes to the production of phenylalanine, but all result in a mixture of products from which phenylalanine must be separated. A suitable feed is the fermentation product of a carbohydrate source, such as sugar, which has been treated by ultrafiltration to remove certain of the impurities such as residual cells, cell debris, etc. The feed may contain, among other components, salts, such as potassium chloride and ammonium phosphate, $(NH_4)_2HPO_4$, sugars, including glucose, and maltose, organic acids, e.g., lactic, phenyllactic acids and hydrocinnamic, amino acids, such as phenyl-alanine, alanine and lysine. The concentration of salts is usually less than 0.1N although in some feeds may be 0.5N or greater. Nevertheless, greater concentrations can be separated in this process since the salts are not adsorbed and eluted at the void volume and recovered in the raffinate.

It is an important aspect of the process to maintain the pH in the range where the phenylalanine is present as a zwitterion and is hydrophobic. At this pH, most of the other components present in the feed will be hydrophilic and will elute at the void volume. The preferred pH will be in the range of 4.5 to 6.5 with a pH of 6 being most preferred.

Illustrative of the adsorbent which may be used in our invention is Amberlite XAD-7, a self-crosslinked homopolymer made from the monomer, trimethylolpropane trimethacrylate, obtained from Rohm & Haas Co. as hard insoluble beads of 20-50 mesh, having a surface area of 450 $m^2/g$, average pore diameter of 80 Å and a porosity of 0.5 to 0.55 ml/g. XAD-8 has a porosity, or pore volume, of 0.52 ml/g, surface area of 140 $m^2/g$, average pore diameter of 235 Å and can be obtained in mesh sizes of 25-50. Since Amberlite XAD-7 and XAD-8 have an aliphatic structure, they are more hydrophilic than other prior art nonionic hydrophobic polymers derived from aromatic monomers, such as the crosslinked polystyrene polymers exemplified by Amberlite XAD-4. Both XAD-7 and XAD-8 have dipole moments of the functional groups of 1.8. Conversely, the dipole moments of the functional groups of XAD-2 and XAD-4, all as reported by Rohm and Haas, the manufacturer, in Summary Bulletin-Amberlite Polymeric Adsorbents (undated), are 0.3. The adsorbents are not limited to those mentioned above, but any other polar, highly porous, crosslinked aliphatic synthetic adsorbent having the same properties can be used.

In the process of the present invention, the fermentation feed mixture containing phenylalanine, salts, carbohydrates, other amino acids and organic acids are brought into contact with a polar hydrophobic crosslinked aliphatic synthetic polymer to thereby adsorb the phenylalanine on said polymeric resin adsorbent and desorbing the phenylalanine adsorbed onto the resin by contacting the adsorbent with a desorbent comprising water, an alcohol, a ketone or an ester, or mixtures thereof. The separation process may be either batch or continuous and preferably in a fixed or moving adsorbent bed system, with the most preferred system being a countercurrent simulated moving bed system, such as described in the aforementioned Broughton U.S. Pat. No. 2,985,589. As previously mentioned, in a typical countercurrent simulated moving bed system, cyclic advancement of the input and output streams are accomplished by a manifolding system, e.g., by rotary disc valves showing U.S. Pat. Nos. 3,040,777 and 3,422,848, in sizes ranging from pilot plant scale to commercial scale.

The instant process represents an improvement over prior art processes in which a non-ionic, non-polar synthetic adsorbent, based on crosslinked polystyrene, was used, as disclosed in the aforementioned U.S. Pat. No. 4,584,400. In Example 2 of said patent, fourteen liters or bed volumes of 1% aqueous ethanol solution was required for elution of the L-phenylalanine. Such a long retention volume is a prohibitive factor in commercialization of such a process; however, utilizing the adsorbent disclosed herein, a greater than 10-fold reduction in retention volume can be achieved, rendering the process commercially viable and quite advantageous. Moreover, with the use of stronger desorbents, such as alcohols, ketones and esters, the retention volume can be reduced even further. For example, alcohols, such as methanol, ethanol, propanol, etc. are suitable. Ketones, such as acetone, methyl ethylketone are also usable. Also, esters, such as ethylacetate, propyl acetate, butyl acetate, etc. are expected to reduce the retention volume by the greatest degree.

A dynamic testing apparatus is employed to test various adsorbents with a particular feed mixture and desorbent material to measure the adsorption characteristics of retention capacity and exchange rate. The apparatus consists of a helical adsorbent chamber of approximately 100 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the adsorbent chamber. A pulse test, performed using this apparatus and the following general procedure, is used to determine data, e.g., selectivity, for various adsorbent systems. The adsorbent is placed in a chamber and filled to equilibrium with a particular desorbent material by passing the desorbent material through the adsorbent chamber. At a convenient time, a pulse of feed containing known concentrations of a tracer and of a particular extract component or of a raffinate component or both, all diluted in desorbent material is injected for a duration of several minutes. Desorbent material flow is resumed, and the tracer and the extract component or the raffinate component (or both) are eluted as in a liquid-solid chromatographic operation. The effluent can be analyzed on-stream or alternatively, effluent samples can be collected periodically and later analyzed separately by analytical equipment and traces of the envelopes or corresponding component peaks developed.

From information derived from the test, adsorbent performance can be rated in terms of void volume, retention volume for an extract or a raffinate component, the rate of desorption of an extract or a raffinate component from the adsorbent, the resolution between the components and selectivity for one component with respect to the other. The retention volume of an extract or a raffinate component may be characterized by the distance between the center of the peak envelope of the extract or raffinate component and the center of the peak envelope of the tracer component (void volume) or some other known reference point. It is expressed in terms of the volume of desorbent material pumped during this time interval represented by the distance between the peak envelopes. The rate of exchange or desorption rate of an extract component with the desorbent material can generally be characterized by the width of the peak envelopes at half intensity. The narrower the peak width, the faster the desorption rate. Selectivity, $\beta$, is determined by the ratio of the net retention volumes of the more strongly adsorbed component to each of the other components.

Resolution is a measure of the degree of separation of a two-component system, and can assist in quantifying the effectiveness of a particular combination of adsorbent, desorbent, conditions, etc. for a particular separation. Resolution for purposes of this application is defined as the distance between the two peak centers divided by the average width of the peaks at ½ the peak height as determined by the pulse tests described hereinafter. The equation for calculating resolution is thus:

$$R = \frac{L_2 - L_1}{1/2(W_1 + W_2)}$$

where $L_1$ and $L_2$ are the distance, in ml, respectively, from a reference point, e.g., zero to the centers of the peaks and $W_1$ and $W_2$ are the widths of the peaks at ½ the height of the peaks.

Although both liquid and vapor phase operations can be used in many adsorptive separation processes, liquid-phase operation is preferred for this process because of the lower temperature requirements and because of the higher yields of extract product than can be obtained with liquid-phase operation over those obtained with vapor-phase operation. Adsorption conditions will include a temperature range of from about 20° C. to about 200° C. with about 50° C. to about 90° C. being more preferred and a pressure range of from about atmospheric to about 500 psig (3450 kPa gauge) being preferred to ensure liquid phase. Desorption conditions will include the same range of temperatures and pressures as used for adsorption.

The examples shown below are intended to further illustrate the process of this invention without unduly limiting the scope and spirit of said process. The examples present test results for various adsorbent and desorbent materials when using the above dynamic testing apparatus.

EXAMPLE I

A pulse test, as described above, was run at 58° C. on a series of feeds comprising 5 ml each of a 2% aqueous solution of each of the following pure components: phenylalanine, lactic acid, phenyllactic acid, glucose and KCl. The adsorbent was Amberlite XAD-7 (Rohm & Haas) having particle sizes of 20–50 mesh. After each feed pulse was introduced, the desorbent water at a pH of 5 was introduced into the column at a flow rate of 2 ml/min. In this example, a total volume of 165 ml water was used to desorb the entire amount of phenylalanine adsorbed onto the adsorbent. The results are shown in the following Table 1.

TABLE 1

| Component Name | Gross Retention Volume (ml) | Net Retention Volume (ml) | Peak Width At Half-Height (ml) | Separation Factor (Beta) | Resolution Factor (0.5 Height) |
|---|---|---|---|---|---|
| KCl | 83.4 | 0 | 16.5 | 1.48 | 1.54 |
| Glucose | 86.1 | 2.7 | 21.9 | 1.44 | 1.31 |
| Lactic | 84.1 | 0.7 | 19.6 | 1.47 | 1.43 |
| PHE lactic | 107.8 | 24.4 | 26.6 | 1.15 | 0.51 |

TABLE 1-continued

| Component Name | Gross Retention Volume (ml) | Net Retention Volume (ml) | Peak Width At Half-Height (ml) | Separation Factor (Beta) | Resolution Factor (0.5 Height) |
|---|---|---|---|---|---|
| PHE | 123.6 | 40.2 | 35.5 | Refer. | Refer. |

EXAMPLE II

Another pulse test was run at 58° C. using an actual fermentation product having the following analysis:

TABLE 2

| Composition | Wt. % |
|---|---|
| Phenylalanine | 2.8 |
| Other Amino Acids (Hydrolyzed) | 0.30 |
| NH₃ | 0.27 |
| Sugars | 0.8 |
| Salts | 1.17 |
| Lactic Acid | 1.0 |
| Phenyllactic Acid | 0.2 |
| Total Solids (%) (Calculated) | 6.5 |
| Total Solids (%) (Measured) | 7.5 |

Feed consisted of 5 ml of the above composition at a pH of 6.1. The desorbent was water at a pH of 7.5 and the flow rate of 2 ml/min. The results are shown in the following Table 3. The amount of water required to completely desorb the phenylalanine was less than 165 ml.

TABLE 3

| Component Name | Gross Retention Volume (ml) | Net Retention Volume (ml) | Peak Width At Half-Height (ml) | Separation Factor (Beta) | Resolution Factor (0.5 Height) |
|---|---|---|---|---|---|
| Salt 1 | 83.2 | 0 | 16.8 | 1.45 | 1.38 |
| Salt 2 | 88.1 | 4.9 | 23.1 | 1.37 | 1.08 |
| Lactic | 90.9 | 7.7 | 13.5 | 1.33 | 1.173 |
| Unknown 1 | 96.6 | 13.4 | 14.5 | 1.25 | 0.93 |
| Unknown 2 | 122.6 | 39.4 | 23 | 0.99 | 0.05 |
| PHE | 121 | 37.8 | 38 | Refer. | Refer. |

EXAMPLE III

Fermentation broth was used in a further pulse test, this time at a pH of 5, using a feed mixture having the composition in the following Table 4. Complete desorption of the phenylalanine required about 175 ml.

TABLE 4

| Composition | Wt. % |
|---|---|
| Phenylalanine | 2.8 |
| Other amino acids (Hydrolyzed) | 0.3 |
| Sugars | 1.1 |
| Salts | 1.66 |
| Lactic Acid | 0.1 |
| Phenyllactic Acid | 0.1 |
| Total Solids (%) (Calculated) | 6.06 |
| Total Solids (%) (Measured-Micro Wave) | 8.1 |

The results are shown in the following Table 5.

TABLE 5

| Component Name | Gross Retention Volume (ml) | Net Retention Volume (ml) | Peak Width At Half-Height (ml) | Separation Factor (Beta) | Resolution Factor (0.5 Height) |
| --- | --- | --- | --- | --- | --- |
| Salt 1 | 81.4 | 0 | 15.4 | 1.51 | 1.39 |
| Salt 2 | 85.8 | 4.4 | 18.7 | 1.43 | 1.18 |
| Lactic | 88.9 | 7.5 | 15.9 | 1.38 | 1.13 |
| PHE lactic | 110.5 | 29.1 | 21 | 1.11 | 0.39 |
| Unknown | 123.4 | 42.0 | 23.4 | 1.00 | 0.01 |
| PHE | 123.1 | 41.7 | 44.3 | Refer. | Refer. |

What is claimed is:

1. A method for separating phenylalanine from a fermentation feed comprising phenylalanine, salts, carbohydrates, amino acids and organic acids, comprising contacting said feed, while maintaining said feed at a pH of about 4.5 to about 6.5, with a hydrophobic, porous synthetic adsorbent having functional groups whose dipole moment is from 1.6 to 2.0, a surface area of 140 to 450 m$^2$/g, an average pore diameter of 80 to 235 Angstroms and a porosity of 0.5 to 0.55 ml/g, comprising a macroporous acrylic ester polymer, adsorbing said phenylalanine onto said adsorbent, removing said other feed components from contact with said adsorbent as raffinate, and desorbing said phenylalanine at desorption conditions with a desorbent comprising water, an alcohol, a ketone or an ester.

2. The method of claim 1 wherein said adsorbent is a crosslinked, macroporous acrylic ester copolymer.

3. The method of claim 2 wherein the crosslinking comonomer is trimethylolpropane trimethacrylate.

4. The method of claim 1 wherein said adsorbent is a crosslinked acrylic ester homopolymer.

5. The method of claim 4 wherein the monomer from which said homopolymer is derived is trimethylolpropane trimethacrylate.

6. The method of claim 1 wherein said desorption conditions comprise temperatures within the range of 40° to 90° C.

7. The method of claim 1 wherein said pH is about 6.

8. The method of claim 1 wherein the concentration of salts in said feed is less than about 0.1N.

9. The method of claim 1 wherein the concentration of salts in said feed is less than about 0.5N.

10. The method of claim 1 wherein the dipole moment of the functional groups of said adsorbent is 1.8.

11. The method of claim 10 wherein the desorbent is water.

12. The method of claim 1 wherein said adsorbent has a surface area of about 450 m$^2$/g, an average pore diameter of about 80 Angstroms, and a porosity of about 0.5 to 0.55 ml/g.

* * * * *